(12) United States Patent
Mukai et al.

(10) Patent No.: US 8,809,061 B2
(45) Date of Patent: Aug. 19, 2014

(54) LIQUID LIVING BODY PHANTOM AND METHOD OF MAKING THE SAME

(75) Inventors: Asuka Mukai, Higashimurayama (JP); Koji Yoshida, Machida (JP)

(73) Assignee: Olympus Corporation, Tokyo (JP)

( * ) Notice: Subject to any disclaimer, the term of this patent is extended or adjusted under 35 U.S.C. 154(b) by 178 days.

(21) Appl. No.: 13/412,228

(22) Filed: Mar. 5, 2012

(65) Prior Publication Data

US 2012/0227478 A1 Sep. 13, 2012

(30) Foreign Application Priority Data

Mar. 8, 2011 (JP) ................................ 2011-050432

(51) Int. Cl.
*G01N 31/00* (2006.01)
*G01N 1/28* (2006.01)
*A61B 8/00* (2006.01)

(52) U.S. Cl.
CPC .............. *G01N 1/2806* (2013.01); *A61B 8/587* (2013.01)
USPC .................. 436/8; 436/19; 436/164; 436/166; 436/172; 436/174; 252/408.1; 73/118.01; 73/865.6; 73/886.4

(58) Field of Classification Search
CPC ......... G01N 1/00; G01N 1/28; G01N 1/2806; A61K 2800/412; A61K 2800/413; A61K 2800/43; A61Q 1/02; A61B 8/587
USPC ............... 436/8, 19, 164, 166, 172, 174, 183; 252/408.1; 73/118.01, 865.6, 866.4
See application file for complete search history.

(56) References Cited

U.S. PATENT DOCUMENTS

| | | | | |
|---|---|---|---|---|
| 5,141,741 | A * | 8/1992 | Ishida et al. ..................... | 424/59 |
| 5,643,557 | A * | 7/1997 | Eteve et al. ..................... | 424/60 |
| 6,318,146 | B1 * | 11/2001 | Madsen et al. ................. | 73/1.86 |
| 6,352,860 | B1 * | 3/2002 | Madsen et al. ..................... | 436/8 |
| 6,635,486 | B2 * | 10/2003 | Madsen et al. ..................... | 436/8 |
| 6,777,240 | B2 * | 8/2004 | Hazen et al. ..................... | 436/8 |
| 6,913,928 | B2 * | 7/2005 | Teta et al. ..................... | 436/8 |
| 7,462,488 | B2 * | 12/2008 | Madsen et al. ..................... | 436/8 |
| 2007/0077216 | A1 * | 4/2007 | Dumousseaux ............... | 424/61 |
| 2010/0209364 | A1 * | 8/2010 | Abe et al. ..................... | 424/59 |

FOREIGN PATENT DOCUMENTS

| | | |
|---|---|---|
| JP | 05-046074 | 2/1993 |
| JP | 2000-199743 | 7/2000 |
| JP | 2008-061909 | 3/2008 |
| JP | 2009-216691 | 9/2009 |

\* cited by examiner

*Primary Examiner* — Maureen Wallenhorst
(74) *Attorney, Agent, or Firm* — Kenyon & Kenyon LLP

(57) ABSTRACT

A living body phantom according to the present invention, which is used as a testing sample in a prepared slide in estimating the performance of a microscope objective lens with the image of the testing sample in the prepared slide acquired by an imaging means via the microscope objective lens and with optical characteristics obtained from the image of the testing sample, includes a non-gel-like solution at least including: a solvent which at least includes water, a refractive index adjustment agent, and a scattering body or which at least includes a refractive index adjustment agent and a scattering body; and a thickener.

16 Claims, 7 Drawing Sheets

LIQUID LIVING BODY PHANTOM AND METHOD OF MAKING THE SAME

This application claims benefits of Japanese Patent Application No. 2011-50432 filed in Japan on Mar. 8, 2011, the contents of which are incorporated by this reference.

BACKGROUND OF THE INVENTION

1. Field of the Invention

This invention relates to a liquid living body phantom which is used as a testing sample in a prepared slide in estimating the performance of a microscope objective lens with the image of the testing sample in the prepared slide which is acquired by an imaging means via the microscope objective lens and with optical characteristics obtained from the image of the testing sample. And, this invention also relates to a method of making the same.

2. Description of the Related Art

Simulated organisms (living body phantoms) which imitate characteristics of living bodies are used for developing apparatuses for examining the influence of electromagnetic wave on living bodies and for measuring a state of and/or the quality of the inside of a living body without destroying the living body, or the like.

Living body phantoms of this type have been disclosed in Japanese Patent TOKUKAI No. 2000-199743, Japanese Patent TOKUKAI No. 2009-216691, Japanese Patent TOKUKAI No. 2008-061909, and Japanese Patent TOKUKAI No. Hei 05-046074 up to now, for example.

The living body phantoms disclosed in Japanese Patent TOKUKAI No. 2000-199743 is a fruit and vegetables-imitating phantom which is used for regulating an object inside quality measurement apparatus for measuring the inside qualities of fruits, vegetables, and so on, in a non-destructive manner. The living body phantoms disclosed in Japanese Patent TOKUKAI No. 2000-199743 consists of a transparent container and a light-transmitting body held by the transparent container. The light-transmitting body consists of water, scattering body, gelling agent, acid, and sugar.

The living body phantoms disclosed in Japanese Patent TOKUKAI No. 2009-216691 is a human body-electromagnetically equivalent phantom which is used for examining and/or studying the influence of electromagnetic waves on human bodies instead of human bodies and the electrical properties to electromagnetic waves of which are equivalent to those of human bodies. The living body phantoms disclosed in Japanese Patent TOKUKAI No. 2009-216691 is made as a solid phantom which includes water and talc $(Mg_3Si_4O_{10}(OH)_2)$, and an agar as a gelling agent is added to the living body phantoms disclosed in Japanese Patent TOKUKAI No. 2009-216691.

The living body phantoms disclosed in Japanese Patent TOKUKAI No. 2008-061909 is a model: which is used for analyzing and/or estimating the influence of electromagnetic waves on living bodies with respect to biological tissues near a power supply coil in the trial manufacture of an energy transmission system for transmitting electrical energy from the outside to a capsule endoscope with the energy transmission system not coming into contact with the capsule endoscopes; and which includes a power supply coil and imitates a human trunk including skin, fat, and muscle. The living body phantoms disclosed in Japanese Patent TOKUKAI No. 2008-061909 consists of deionized water, polyethylene powder as a gelling agent, sodium chloride, thickener, and boric acid and is held by a cylinder-shaped polypropylene container.

As described above, gelling agents are used for the living body phantoms which are disclosed in Japanese Patent TOKUKAI No. 2000-199743, Japanese Patent TOKUKAI No. 2009-216691, Japanese Patent TOKUKAI No. 2008-061909.

The living body phantoms disclosed in Japanese Patent TOKUKAI No. Hei 05-046074 is a phantom which is used for electrically faithfully simulating animals and plants. In the living body phantoms disclosed in Japanese Patent TOKUKAI No. Hei 05-046074, liquid obtained by uniformly mixing electrolyte aqueous solution or pure water with monohydric alcohol or polyalcohol which is a polar organic compound is enclosed in a container the electromagnetic wave transmittance of which is 0.9 or more.

SUMMARY OF THE INVENTION

Now, microscope objective lenses have been estimated with the images of testing samples in prepared slides which are acquired by an imaging means via the microscope objective lenses and with optical characteristics obtained from the images of the testing samples.

The use of living body phantoms as a simulated organism substituted for living bodies or as a testing sample in a prepared slide in estimating microscope objective lenses is studied. It is desired that such living body phantoms maintain the same properties as living bodies have, for a long period. And, it is desired that the motions of observation objects such as particles are controlled to the extent that an image is not blurred even though the image is acquired through an imaging means, in such living body phantoms.

A liquid living body phantom according to the present invention, which is used as a testing sample in a prepared slide in estimating the performance of a microscope objective lens with the image of the testing sample in the prepared slide acquired by an imaging means via the microscope objective lens and with optical characteristics obtained from the image of the testing sample, is characterized in that the liquid living body phantom includes a non-gel-like solution, the non-gel-like solution at least including: a solvent which at least includes water, a refractive index adjustment agent, and a scattering body or which at least includes a refractive index adjustment agent and a scattering body; and a thickener.

Also, in a liquid living body phantom according to the present invention, it is preferred that the non-gel-like solution has a viscosity of 40 mPa·s or more and 300 mPa·s or less at a temperature of 20° C.

Also, in a liquid living body phantom according to the present invention, it is preferred that the non-gel-like solution has a viscosity of 50 mPa·s or more and 100 mPa·s or less at a temperature of 20° C.

Also, in a liquid living body phantom according to the present invention, it is preferred that an amount of the added thickener is a predetermined amount in which the proportion of the mass of the thickener to the mass of the solvent is 0.5 or more and is 3 or less when the mass of the solvent is 100.

Also, in a liquid living body phantom according to the present invention, it is preferred that the liquid living body phantom further includes a fluorescent substance.

Also, in a liquid living body phantom according to the present invention, it is preferred that the living body phantom has an optical characteristic which is equivalent to at least one optical characteristic of a living body which is one of a refractive index, a scattering coefficient, an absorption coefficient, and an anisotropic scattering parameter.

Also, in a liquid living body phantom according to the present invention, it is preferred that the scattering body is a sphere-shaped particle.

Also, in a liquid living body phantom according to the present invention, it is preferred that the particle diameter of the scattering body is 100 nm or more and is 10 μm or less.

Also, in a liquid living body phantom according to the present invention, it is preferred that the fluorescent substance is fluorescent microsphere.

Also, in a liquid living body phantom according to the present invention, it is preferred that the fluorescent microsphere has the same particle diameter and the same shape as the scattering body does.

A method of making a liquid living body phantom according to the present invention is characterized in that the method includes: a first step of making a solvent by uniformly mixing water, a refractive index adjustment agent, and a scattering body with one another or by uniformly mixing a refractive index adjustment agent and a scattering body with each other; and a second step of making a non-gel-like solution which has a viscosity of 40 mPa·s or more and 300 mPa·s or less at a temperature of 20° C., by adding a predetermined amount of thickener to the solvent made in the first process in such a way that the proportion of the mass of the thickener to the mass of the solvent is 0.5 or more and is 3 or less when the mass of the solvent is 100.

Also, in a method of making a liquid living body phantom according to the present invention, it is preferred that the non-gel-like solution having a viscosity of 50 mPa·s or more and 100 mPa·s or less at a temperature of 20° C. is made in the second step.

Also, in a method of making a liquid living body phantom according to the present invention, it is preferred that a fluorescent substance is uniformly mixed with the water, the refractive index adjustment agent, and the scattering body or with the refractive index adjustment agent and the scattering body in the first process.

Also, in a method of making a liquid living body phantom according to the present invention, it is preferred that the scattering body is a sphere-shaped particle.

Also, in a method of making a liquid living body phantom according to the present invention, it is preferred that the particle diameter of the scattering body is 100 nm or more and is 10 μm or less.

Also, in a method of making a liquid living body phantom according to the present invention, it is preferred that the fluorescent substance is fluorescent microsphere.

Also, in a method of making a liquid living body phantom according to the present invention, it is preferred that the fluorescent microsphere has the same particle diameter and the same shape as the scattering body does.

According to the present invention, the ranges of the movements of observation objects such as particles in a living body phantom can be controlled to the extent that the images of the observation objects are not blurred, without adding a gelling agent to the living body phantom. Accordingly, the present invention makes it possible to calibrate apparatuses in which there are no variations in characteristics, in which the characteristics are even ones, in which chronological changes in the characteristics are extremely small, and by which reliable measurement data are obtained, and/or the present invention makes it possible to estimate the performance of these apparatuses. And, there is no necessity that living body phantoms according to the present invention should be made as often as measurement is performed, and living body phantoms according to the present invention can be reused repeatedly. Also, living body phantoms according to the present invention can maintain their characteristics for half a year or more after making the living body phantoms. Living body phantoms according to the present invention can be preserved in a container for the preservation of and/or carry of phantoms for a long time and can be carried through the container, without the decay of the living body phantoms. Living body phantoms according to the present invention are easy to handle and do not require a selection from sample shapes. In addition, it is possible to make a fine adjustment of the characteristics of living body phantoms according to the present invention by adding water to the living body phantoms in the case where water evaporates from the living body phantoms, so that the living body phantoms can reproduce characteristics nearer to those of living bodies. In living body phantoms according to the present invention, it is possible to make observation objects such as particles in observation approximately immovable, so that the living body phantoms requires neither cooling of the living body phantoms for gelling (solidification) nor polymer coating. As a result, the present invention makes it possible to simplify a process of making a phantom, makes it possible to shorten time necessary for making a phantom, and makes it possible to reduce costs, so that liquid living body phantoms the industrial utility value of which increases can be obtained.

These and other features and advantages of the present invention will become apparent from the following detailed description of the preferred embodiments when taken in conjunction with the accompanying drawings.

BRIEF DESCRIPTION OF THE DRAWINGS

FIG. 1 is an explanatory view showing a prepared slide which is prepared with a living body phantom for each of embodiments and a comparative example in the present invention.

DETAILED DESCRIPTION OF THE PREFERRED EMBODIMENTS

Figure 1A:
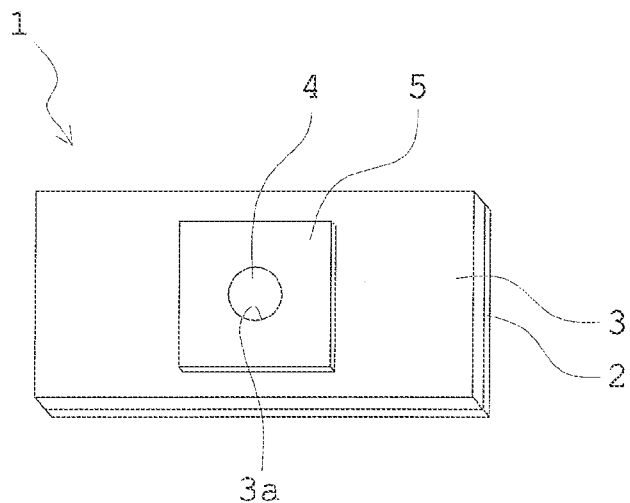
FIG. 1A is a plane view of the prepared slide.

Gelling agents as disclosed in Japanese Patent TOKUKAI No. 2000-199743, Japanese Patent TOKUKAI No. 2009-216691, and Japanese Patent TOKUKAI No. 2008-061909 are added to living body phantoms which imitate the characteristics of living bodies in order that the living body phantoms reproduce the characteristics of living bodies. As a result, a very large number of solid living body phantoms in which particles are immovable have been reported. In particular, a very large number of living body phantoms with gelling agents such as agar are considered in order that the living body phantoms reproduce real tactile sensations and real shapes of living bodies.

However, such solid living body phantoms have a problem that the characteristics of the solid living body phantoms widely vary due to evaporation of water and such solid living body phantoms are not adequate to the long preservation of the phantoms.

On the other hand, in the liquid living body phantom which is disclosed in Japanese Patent TOKUKAI No. Hei 05-046074 and to which no gelling agent is added, observation objects such as particles in a solution which constitute the living body phantom is not made to stand immovable as described above, so that the moving speeds of and the ranges of the movements of the observation objects such as particles increase and acquired images are inevitably blurred.

However, there is no necessity that the observation objects such as particles in the living body phantoms should be immovable. If the observation objects such as particles are immovable in measuring and/or estimating the living body phantom, it is possible to measure and/or estimate the living body phantom practically.

Particles which are usually used as an observation object for living body phantoms are colloid particles and always move in liquid through Brownian motion. The movements of the particles are expressed by the following formula (1):

$$A = K\sqrt{\frac{\tau TR}{\eta Nr}} \quad (1)$$

where, A denotes oscillations of particles performing Brownian motion, K denotes a constant, $\eta$ denotes the viscosity of the solution, N denotes the number of the particles in 1 g of solution, r denotes the radiuses of the particles, $\tau$ denotes a period of Brownian motion, T denotes absolute temperature, and R denotes the gas constant. It is found from the formula (1) that the oscillations A of the particles performing Brownian motion are inversely proportional to the square root of the viscosity $\eta$ of the solution. Accordingly, when the viscosity $\eta$ of the solution is increased by a thickener, it is possible to control the oscillations A of the particles performing Brownian motion.

Also, when polymers like thickener are added to sol or the like in which particles disperse, the polymers adhere to the surfaces of the particles, so that the diffusion motions of the particles are controlled. As a result, the particles can be regarded as one large aggregate, from macroscopic point of view. Accordingly, when the Brownian motion of the particles can be controlled even though the particles are not made to stand immovable unlike gel, it is possible to achieve a state in which the particles are approximately immovable.

A value of the viscosity $\eta$ of the solution which is necessary for controlling the oscillations A of the particles performing Brownian motion is determined in accordance with apparatuses used for measuring and/or estimating living body phantoms or in accordance with required accuracy. For example, the solution should be made to have a viscosity η of 50 mPa·s or more at a temperature of 20° C. in the case where fluorescent particles in a living body phantom are observed for 30 seconds.

That is to say, in a liquid living body phantom according to the present invention, it is desirable that the solution has a viscosity η of 40 mPa·s or more and 300 mPa·s or less at a temperature of 20° C. In addition, it is more desirable that the solution has a viscosity η of 50 mPa·s or more and 100 mPa·s or less at a temperature of 20° C.

Besides, thickeners used for liquid living body phantoms according to the present invention are not limited in particular, and a thickener may be freely selected from commercial thickeners such as xanthan gum and may be used for the present invention.

Also, in order that the viscosity η of the solution of a liquid living body phantom made by using such thickeners is in such an above-described range, it is desirable that an amount of the thickener added to a liquid living body phantom according to the present invention is an amount in which the proportion of the mass of the thickener to the mass of the solvent is 0.5 or more and is 3.0 or less, more preferably, is 0.5 or more and is 1.0 or less when the mass of the solvent consisting of water, refractive index adjustment agent, and scattering body or consisting of refractive index adjustment agent and scattering body is 100, for example.

If the proportion of the mass of the thickener to the mass of the solvent is smaller than 0.5 when the mass of the solvent is 100, the viscosity η of the solution does not have a value necessary for making the particles immovable. On the other hand, if the proportion of the mass of the thickener to the mass of the solvent is larger than 3.0 when the mass of the solvent is 100, the thickener cannot be dissolved in the solvent, so that the characteristics of an obtained living body phantom inevitably become uneven (unevenness of the characteristics occurs).

Also, a liquid living body phantom according to the present invention may further include a fluorescent substance. A liquid living body phantom including a fluorescent substance can be used for estimating and/or calibrating microscope objective lenses for apparatuses for fluorescent measurement such as fluorescent microscopes and two-photon microscopes.

Also, a liquid living body phantom according to the present invention has an optical characteristic which is equivalent to at least one optical characteristic of a living body which is one of a refractive index, a scattering coefficient, an absorption coefficient, and an anisotropic scattering parameter (g parameter).

The optical characteristics of living bodies are determined mainly by refractive indices of mediums, the scattering by organelles or the like, and, the absorption into blood vessels or the like. Accordingly, it is possible to obtain living body phantoms reproducing optical characteristics of living bodies better by making each of the living body phantoms have an optical characteristic equivalent to at least one of these optical characteristics.

Also, in a liquid living body phantom according to the present invention, it is desirable that the scattering body in the solution is a sphere-shaped particle.

The use of the sphere-shaped particle makes it possible to make liquid living body phantoms which have high uniformity as compared with the use of an ellipse-shaped or needle-shaped particle. In addition, it is possible to control optical characteristics of living bodies such as a scattering coefficient and an anisotropic scattering parameter (g parameter) with good reproducibility of these optical characteristics.

Also, in a liquid living body phantom according to the present invention, it is desirable that the particle diameter of the scattering body is 100 nm or more and is 10 μm or less.

Scattering bodies affecting the optical characteristics of a living body in its cells are originated from organelles such as nucleus and endoplasmic reticulum, and the sizes of these organelles approximately range from 100 nm to 10 μm. Accordingly, when a particle having a particle diameter in this range is used as a scattering body, it is possible to make a living body phantom which has characteristics nearer to the characteristics of a real living body.

Also, in a liquid living body phantom according to the present invention, it is desirable that the fluorescent substance in the solution is fluorescent microsphere.

The use of fluorescent microsphere makes it possible to verify: whether the sample can be accurately observed or not while the real shape of and the real size of the sample under fluorescence observation are being unchanged; and what resolution is acquired in the sample, in the above-described apparatuses for fluorescence measurement. Up to now, there exists no sample which can be estimated in such a manner.

Also, it is desirable that the fluorescent microsphere for a liquid living body phantom according to the present invention has the same particle diameter and the same shape as the scattering body does.

Because a scattering characteristic widely varies with the particle diameter of and the shape of a scattering body, the use of fluorescent microsphere having the same particle diameter and the same shape as the scattering body makes it possible to keep the influence on the scattering characteristic of a living body phantom according to the present invention to a minimum.

Embodiments

The embodiments for liquid living body phantoms according to the present invention are explained below.

<Preparation of Phantom>

Material

In making liquid living phantoms of the embodiments 1 to 3, the following materials were used. Besides, water is not used in preparing a solvent in making the liquid living body phantoms of the embodiment 3.

Water: Ultra pure water
  Refractive index adjustment agent: Glycerin for fluorescence microscopes (Made by Merck LTD.)
  Scattering body: Particles having standard particle diameters (water dispersion) 3500A (Made by Thermo Fisher Scientific)
  Thickener: Xanthan Gum XANTHAN G (Made by SAN-SHO CO., LTD)
  Fluorescent body: Fluorescent particles (water dispersion) G500 (Made by Duke Scientific Corp.)

Also, in making a living body phantom of the comparative example 1, the following material was used instead of the thickener of the above-described materials Gelling agent: Seakem HGT Agarose (Made by TAKARA BIO., INC)

Procedure for Making Phantom

The living body phantoms of the embodiments 1 to 3 were made with the above-described materials in the following manner:

(1) First, glycerin and water are weighed in a sample bottle and are stirred until the glycerin and water are uniformly mixed with each other. Besides, in the case where the below-described liquid living body phantom of the embodiment 3 is made, only glycerin is weighed in a sample bottle and the glycerin is not mixed with water.

(2) Next, a scattering body which has been weighed is added to the liquid which has undergone the process (1), and the solution added the scattering body is stirred until the solution is uniformly mixed with the scattering body (Besides, in the case where a living body phantom including a fluorescent body is made, the fluorescent body, together with the scattering body, is weighed and added to the solution at this stage, and then the solution to which the fluorescent body together with the scattering body is added is stirred).

(3) Next, a thickener is weighed on a medical paper.

(4) Next, the thickener which has been weighed in the process (3) is added to the liquid which has undergone the process (2) little by little while the solution having undergone the process (2) is being stirred.

(5) Next, after the whole of the thickener is added to the liquid which has undergone the process (2), the liquid is stirred (for three hours or more) until the thickener is uniformly dissolved in the liquid, so that a solution of living body phantom is finished.

Besides, the viscosity of the finished solution of living body phantom was measured with a laboratory handy-type digital viscometer (made by MARUYASU INDASTRIES CO., LTD), and it was verified that the viscosity of the solution at a temperature of 20° C. was 40 mPa·s or more and was 300 mPa·s or less.

<Evaluation of Characteristics of Phantom>

Refractive Index

The refractive indices of the prepared living body phantoms at a temperature of 25° C. were measured with a digital refractometer (made by ATAGO CO., LTD), When the refractive indices of the prepared living body phantoms were measured, prepared slides enough to perform measurement were provided in advance in a below-described test of the preservability of living body phantoms put in prepared slides, and one prepared slide was used per measurement. The prepared slides were made in such a way that: each of the liquid living body phantoms was poured into a hole in a silicon rubber with which the upper plane of a glass slide was coated; and then the upper plane of the silicon rubber was covered with a cover glass. For example, in the case where it is desired that ten samples of liquid living body phantoms which are put in prepared slides are measured every five minutes in order to examine the chronological change in the liquid living body phantoms, ten prepared slides (No. 1 to No. 10) are first made together, and then a living body phantom is taken from a prepared slide corresponding to each of points in elapsed time and then is measured, in such a way that the prepared slide No. 1 is measured in five minutes, the prepared slide No. 2 is measured in ten minutes, and so on.

Also, in the below-described test of the preservability of living body phantoms stored in containers, the living body phantoms were taken from containers in which the living body phantoms were stored respectively, and then the living body phantoms were measured.

Scattering Coefficient

The scattering coefficients of the prepared living body phantoms were calculated by measuring the intensity of incident light and the intensity of transmitted light when the length of the optical path was L and by using the following formula (2):

$$I = I_0 \exp(-\mu_s L) \quad (2)$$

where $I_0$ denotes the intensity of incident light, I denotes the intensity of transmitted light, $\mu_s$ denotes the scattering coefficients, and L denotes the length of optical path.

Besides, measurement of the light intensities for each of the living body phantoms was performed after each of the living body phantoms was taken from the container in which each of the living body phantoms was stored.

Embodiment 1

Figure 1B:
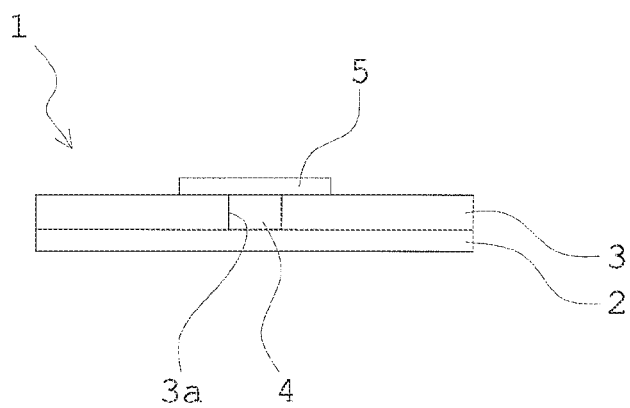
FIG. 1B is a cross sectional view of the prepared slide.
Figure 2:
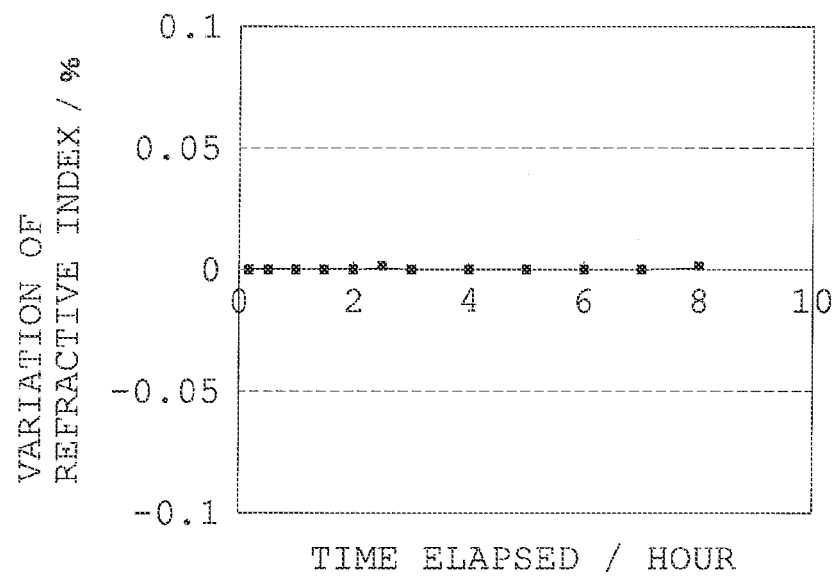
FIG. 2 is a graph showing a characteristic of a liquid living body phantom of the embodiment 1 on variation of refractive index to elapsed time in the case where a prepared slide which is prepared with the liquid living body phantom of the embodiment 1 as shown in FIG. 1 and in which the liquid living body phantom of the embodiment 1 is put is placed at rest at room temperature.
Figure 3:
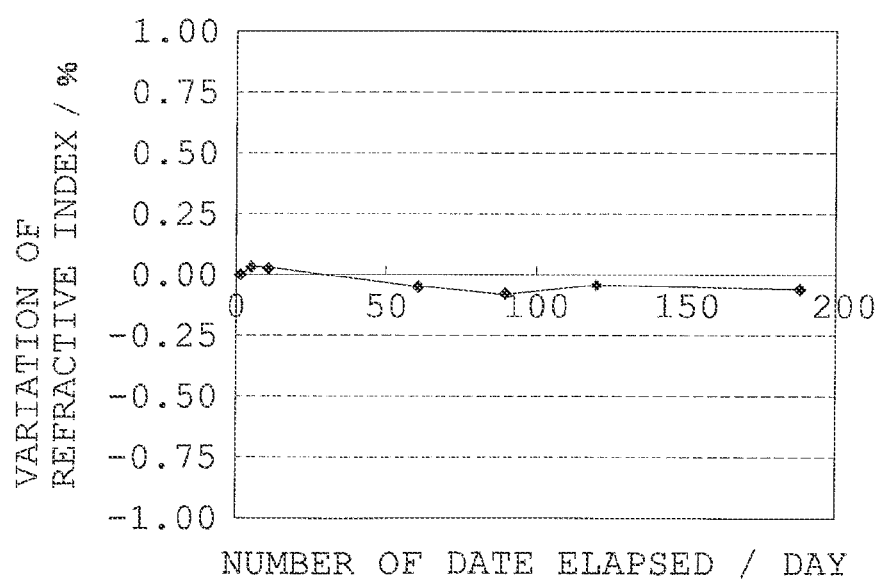
FIG. 3 is a graph showing a characteristic of the liquid living body phantom of the embodiment 1 on variation of refractive index to elapsed days in the case where the liquid living body phantom of the embodiment 1 is put in an airtight container and the airtight container is in an environment in which the regulation for keeping temperature and/or humidity constant is not performed so that a state of the storage of the liquid living body phantom does not become steady.
Figure 4:
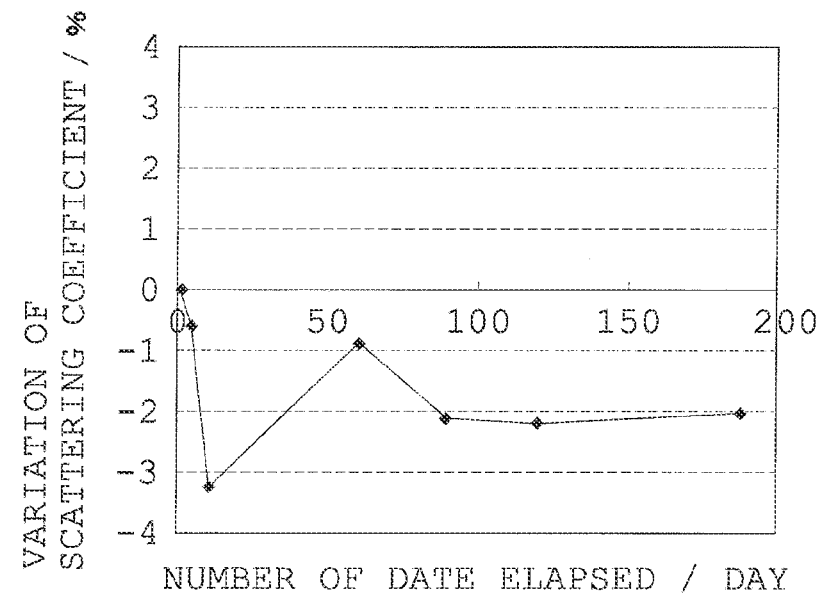
FIG. 4 is a graph showing a characteristic of the liquid living body phantom of the embodiment 1 on variation of scattering coefficient to elapsed days in the case where the liquid living body phantom of the embodiment 1 is put in an airtight container and the airtight container is in an environment in which the regulation for keeping temperature and/or humidity constant is not performed so that a state of the storage of the liquid living body phantom does not become steady.

FIG. 1 is an explanatory view showing a prepared slide which is prepared with a living body phantom for each of the embodiments 1 to 3 and the comparative example 1 in the present invention, FIG. 1A is a plane view of the prepared slide, and FIG. 1B is a cross sectional view of the prepared slide. FIG. 2 is a graph showing a characteristic of a liquid living body phantom of the embodiment 1 on variation of refractive index to elapsed time in the case where a prepared slide which is prepared with the liquid living body phantom of the embodiment 1 as shown in FIG. 1 and in which the liquid living body phantom of the embodiment 1 is put is placed at rest at room temperature. FIG. 3 is a graph showing a characteristic of the liquid living body phantom of the embodiment 1 on variation of refractive index to elapsed days in the case where the liquid living body phantom of the embodiment 1 is put in an airtight container and the airtight container is in an environment in which the regulation for keeping temperature and/or humidity constant is not performed so that a state of the storage of the liquid living body phantom does not become steady. FIG. 4 is a graph showing a characteristic of the liquid living body phantom of the embodiment 1 on variation of scattering coefficient to elapsed days in the case where the liquid living body phantom of the embodiment 1 is put in an airtight container and the airtight container is in an environment in which the regulation for keeping temperature and/or humidity constant is not performed so that a state of the storage of the liquid living body phantom does not become steady.

The liquid living body phantom of the embodiment 1 was made by mixing the above-described materials with one another on the basis of a material composition ratio shown in Table 1 and by stirring these materials. The viscosity η of the solution is as shown in Table 1.

Thickener and fluorescent body were added to a solvent consisting of water, refractive index adjustment agent, and scattering body in such a way that the proportion of the mass of the thickener to the total mass of the solvent composed of these three constituents and the proportion of the mass of the fluorescent body to the total mass of the solvent composed of these three constituents were 0.5 and 1 respectively when the total mass of the solvent consisting of these three constituents is 100.

Preservability of Liquid Living Body Phantom Put in Prepared Slide

A prepared slide which is shown in FIG. 1 was made with the prepared liquid living body phantom of the embodiment 1, and the prepared slide was placed at rest at room temperature (at a temperature of 23° C. in this case). The prepared slide 1 was made in such a way that: the liquid living body phantom 4 was poured into a hole 3a provided for a silicon rubber 3 with which the upper plane of a glass slide 2 was coated and the thickness of which was about 2 mm; and then the upper plane of the portion of the silicon rubber 3 into which the liquid living body phantom 4 was poured was covered with a cover glass 5. The refractive index of the liquid living body phantom 4 was measured in a chronological manner after the prepared slide 1 was made. As a result, the result as shown in FIG. 2 was obtained. As shown in FIG. 2, it was verified that the refractive index of the liquid living body phantom of the embodiment 1 was maintained even after eight hours had passed from the preparation of the prepared slide.

Preservability of Liquid Living Body Phantom Stored in Container

Also, the prepared liquid living body phantom of the embodiment 1 was put in an airtight container, and the airtight container was stored in an environment in which the regulation for keeping temperature and/or humidity constant was not performed so that a state of the storage of the liquid living body phantom did not become steady.

The measurement results of the refractive index and the scattering coefficient of the liquid living body phantom of the embodiment 1 stored in the airtight container relative to elapsed days are shown in FIGS. 3 and 4 respectively, in the form of variation amount.

As shown in FIGS. 3 and 4, it was verified that: the liquid living body phantom of the embodiment 1 could be preserved even under a rough condition in which a state of the storage of the liquid living body phantom is not steady in an environment in which the regulation for keeping temperature and/or humidity constant is not performed; the liquid living body phantom of the embodiment 1 was not changed in quality; and the approximately same characteristics as the liquid living body phantom of the embodiment 1 originally had could be maintained even after half of a year had passed from the preparation of the liquid living body phantom of the embodiment 1 (the variations in the refractive index and the scattering coefficient are refractive index±0.1% or less and scattering coefficient±4% or less, respectively).

Reproducibility of Optical Characteristics in Liquid Living Body Phantom

Besides, the reproducibility of the optical characteristics in liquid living body phantoms that were made with the same composition and in the same preparation manner was also tested in the embodiment 1.

The detailed explanation is as follows. A plurality of liquid living body phantoms (for example, five living body phantoms) having the composition shown in the embodiment 1 were made. Each of the prepared liquid living body phantoms was put in each of airtight containers, the airtight containers were stored in an environment in which the regulation of keeping temperature and/or humidity constant did not performed so that a state of the storage of the liquid living body phantoms did not become steady, and then the refractive indices and scattering coefficients of these liquid living body phantoms were measured as days passed.

And, the refractive indices and scattering coefficients of the liquid living body phantoms of the embodiment 1 that were put and stored in the containers were measured until 200 days passed just after the liquid living body phantoms of the embodiment 1 were put and stored in the containers, and the variations in the measured refractive indices and the measured scattering coefficients relative to elapsed days were calculated. The calculation results just after the liquid living body phantoms of the embodiment 1 were made are shown in Table 2. Besides, it was verified that the variations in the refractive indices and the scattering coefficients changed in the range of the values of the refractive indices and the scattering coefficients which the liquid living body phantoms had just after the liquid living body phantoms were made, all the time until 200 days passed.

As shown in Table 2, the liquid living body phantom of the embodiment 1 has the small variations in its optical characteristics due to the preparation of the liquid living body phantom and has a good reproducibility.

Deviations of Optical Characteristics of Liquid Living Body Phantom from Target Values In addition, the deviation rates of the optical characteristics of the prepared liquid living body phantoms from target values were also calculated in the embodiment 1.

The detailed explanation is as follows. The refractive indices and scattering coefficients which the liquid living body phantoms of the embodiment 1 had just after the liquid living body phantoms of the embodiment 1 were made were measured, and the deviation rates of the measured refractive indices and the measured scattering coefficients from target values were calculated when the refractive index and the scattering coefficient of a predetermined living body for which the liquid living body phantoms of the embodiment 1 were used as a simulated object were used as the target values. The calculation results are shown in Table 2.

As shown in Table 2, both of the deviations of the refractive index and the scattering coefficient of the liquid living body phantom of the embodiment 1 from the target values are small and the liquid living body phantom of the embodiment 1 has high reliability as a simulated organism.

Embodiments 2 and 3

Figure 5:
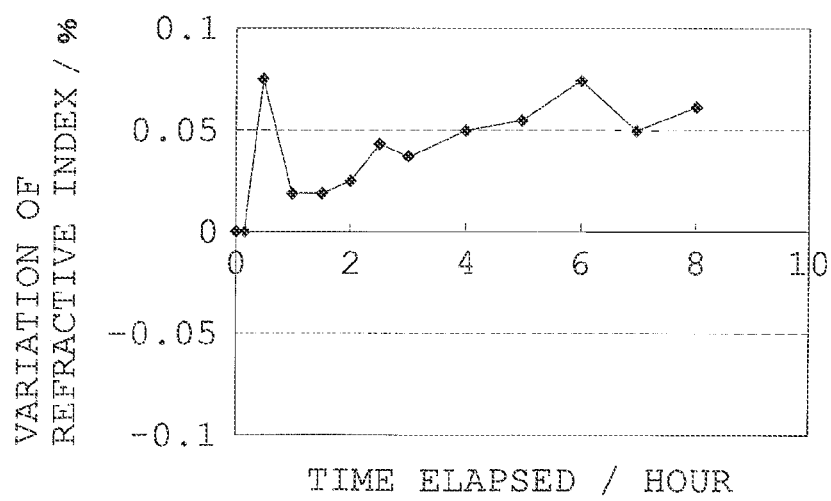
FIG. 5 is a graph showing a characteristic of a liquid living body phantom of the embodiment 2 on variation of refractive index to elapsed time in the case where a prepared slide which is prepared with the liquid living body phantom of the embodiment 2 as shown in FIG. 1 and in which the liquid living body phantom of the embodiment 2 is put is placed at rest at room temperature.
Figure 6:
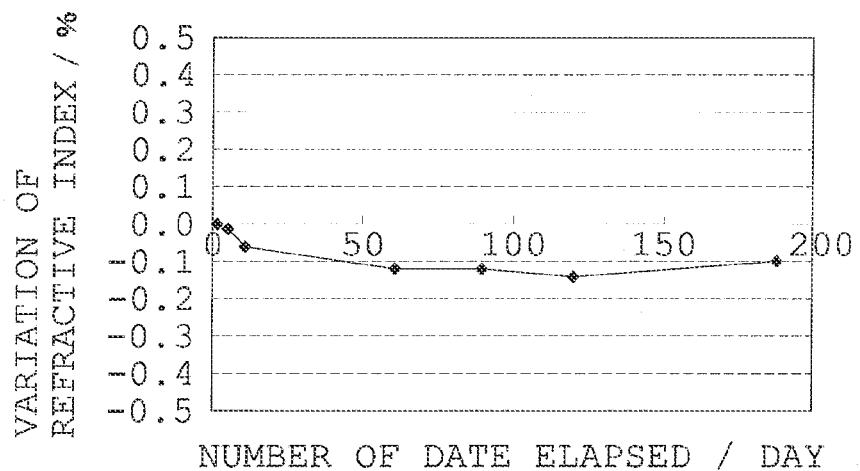
FIG. 6 is a graph showing a characteristic of the liquid living body phantom of the embodiment 2 on variation of refractive index to elapsed days in the case where the liquid living body phantom of the embodiment 2 is put in an airtight container and the airtight container is in an environment in which the regulation for keeping temperature and/or humidity constant is not performed so that a state of the storage of the liquid living body phantom does not become steady.
Figure 7:
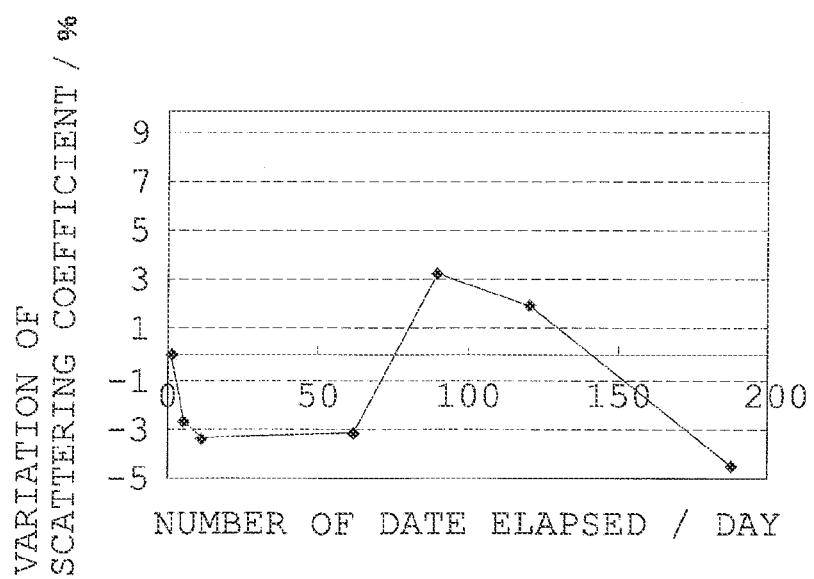
FIG. 7 is a graph showing a characteristic of the liquid living body phantom of the embodiment 2 on variation of scattering coefficient to elapsed days in the case where the liquid living body phantom of the embodiment 2 is put in an airtight container and the airtight container is in an environment in which the regulation for keeping temperature and/or humidity constant is not performed so that a state of the storage of the liquid living body phantom does not become steady.
Figure 8:
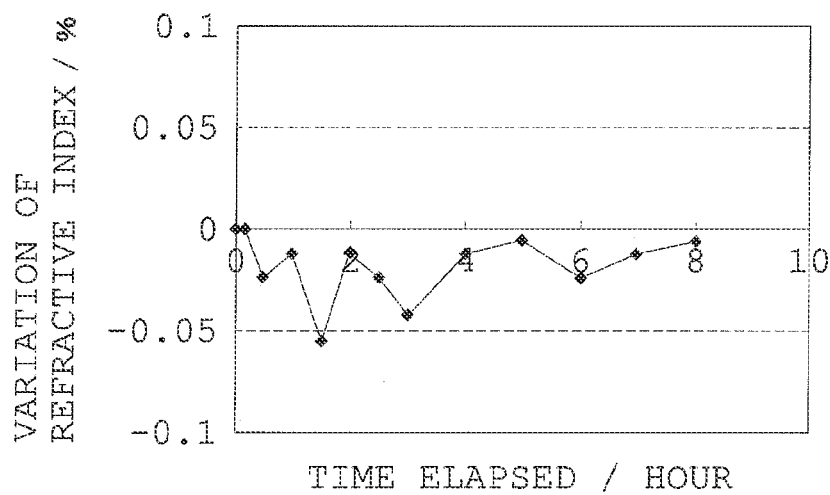
FIG. 8 is a graph showing a characteristic of a liquid living body phantom of the embodiment 3 on variation of refractive index to elapsed time in the case where a prepared slide which is prepared with the liquid living body phantom of the embodiment 3 as shown in FIG. 1 and in which the liquid living body phantom of the embodiment 3 is put is placed at rest at room temperature.
Figure 9:
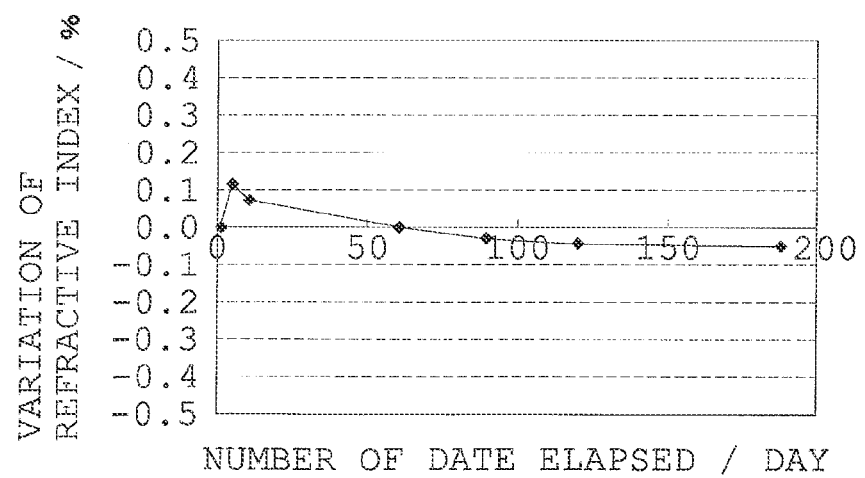
FIG. 9 is a graph showing a characteristic of the liquid living body phantom of the embodiment 3 on variation of refractive index to elapsed days in the case where the liquid living body phantom of the embodiment 3 is put in an airtight container and the airtight container is in an environment in which the regulation for keeping temperature and/or humidity constant is not performed so that a state of the storage of the liquid living body phantom does not become steady.
Figure 10:
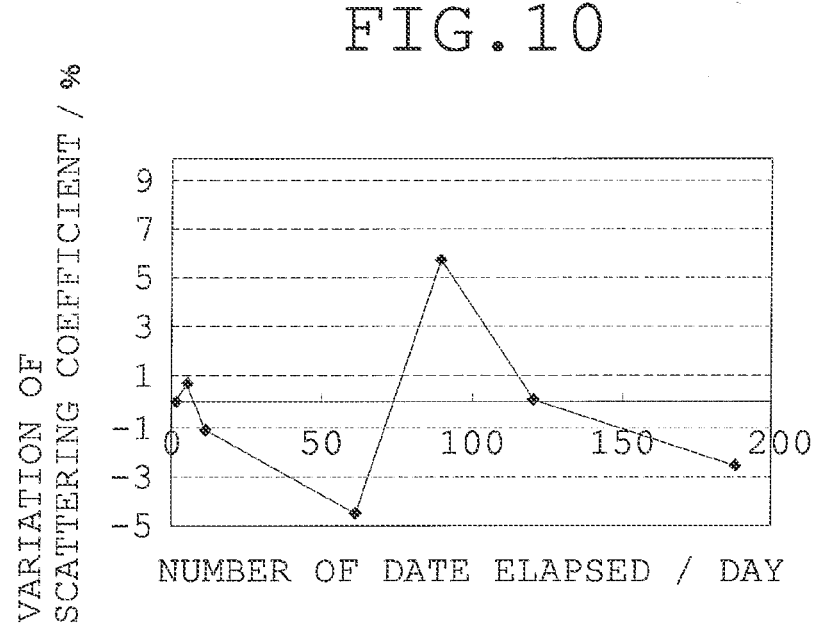
FIG. 10 is a graph showing a characteristic of the liquid living body phantom of the embodiment 3 on variation of scattering coefficient to elapsed days in the case where the liquid living body phantom of the embodiment 3 is put in an airtight container and the airtight container is in an environment in which the regulation for keeping temperature and/or humidity constant is not performed so that a state of the storage of the liquid living body phantom does not become steady.

FIG. 5 is a graph showing a characteristic of a liquid living body phantom of the embodiment 2 on variation of refractive index to elapsed time in the case where a prepared slide which is prepared with the liquid living body phantom of the embodiment 2 as shown in FIG. 1 and in which the liquid living body phantom of the embodiment 2 is put is placed at rest at room temperature. FIG. 6 is a graph showing a characteristic of the liquid living body phantom of the embodiment 2 on variation of refractive index to elapsed days in the case where the liquid living body phantom of the embodiment 2 is put in an airtight container and the airtight container is in an environment in which the regulation for keeping temperature and/or humidity constant is not performed so that a state of the storage of the liquid living body phantom does not become steady. FIG. 7 is a graph showing a characteristic of the liquid living body phantom of the embodiment 2 on variation of scattering coefficient to elapsed days in the case where the liquid living body phantom of the embodiment 2 is put in an airtight container and the airtight container is in an environment in which the regulation for keeping temperature and/or humidity constant is not performed so that a state of the storage of the liquid living body phantom does not become steady. FIG. 8 is a graph showing a characteristic of a liquid living body phantom of the embodiment 3 on variation of refractive index to elapsed time in the case where a prepared slide which is prepared with the liquid living body phantom of the embodiment 3 as shown in FIG. 1 and in which the liquid living body phantom of the embodiment 3 is put is placed at rest at room temperature. FIG. 9 is a graph showing a characteristic of the liquid living body phantom of the embodiment 3 on variation of refractive index to elapsed days in the case where the liquid living body phantom of the embodiment 3 is put in an airtight container and the airtight container is in an environment in which the regulation for keeping temperature and/or humidity constant is not performed so that a state of the storage of the liquid living body phantom does not become steady. FIG. 10 is a graph showing a characteristic of the liquid living body phantom of the embodiment 3 on variation of scattering coefficient to elapsed days in the case where the liquid living body phantom of the embodiment 3 is put in an airtight container and the airtight container is in an environment in which the regulation for keeping temperature and/or humidity constant is not performed so that a state of the storage of the liquid living body phantom does not become steady.

The liquid living body phantoms of the embodiments 2 and 3 were made on the basis of a material composition ratio shown in Table 1 in the same manner as in the embodiment 1. Also, as in the embodiment 1, the refractive indices and the scattering coefficients of the liquid living body phantoms of the embodiments 2 and 3 were measured in order to examine the preservabilities of the liquid living body phantoms of the embodiments 2 and 3 that were put in prepared slides or stored in airtight containers. When the liquid living body phantoms of the embodiments 2 and 3 were stored, as in the embodiment 1, the prepared liquid living body phantoms of the embodiment 2 and 3 were put in airtight containers respectively, and the airtight containers were stored in an environment in which the regulation for keeping temperature and/or humidity constant was not performed so that a state of the storage of the liquid living body phantoms did not become steady.

The measurement results of the refractive indices and the scattering coefficients of the liquid living body phantoms of the embodiments 2 and 3 put in the prepared slides or stored in the airtight containers relative to elapsed time and elapsed days are shown in FIGS. 5 to 10 respectively, in the form of variation amount.

As shown in FIGS. 5 to 7 (the embodiment 2) and in FIGS. 8 to 10 (the embodiment 3), it was verified that: the chronological change of each of the liquid living body phantoms of the embodiments 2 and 3 was extremely small; and each of the liquid living body phantoms of the embodiment 2 and 3 had the stability of the long preservation of each of the liquid living body phantoms of the embodiments 2 and 3, as in the embodiment 1.

Also, the reproducibility of the optical characteristics in liquid living body phantoms that were made with the same composition and/or in the same preparation manner was also tested in the embodiment 2 in the same manner as in the embodiment 1.

The refractive indices and scattering coefficients of the liquid living body phantoms of the embodiment 2 that were put and stored in airtight containers were measured until 200 days passed just after the liquid living body phantoms of the embodiment 2 were put and stored in the containers respectively, and the variations in the measured refractive indices and the measured scattering coefficients relative to elapsed days were calculated. The calculation results just after the liquid living body phantoms of the embodiment 2 were made are shown in Table 2. Besides, also in the embodiment 2 as in the embodiment 1, it was verified that the variations in the refractive indices and the scattering coefficients changed in the range of the values of the refractive indices and the scattering coefficients which the liquid living body phantoms of the embodiment 2 had just after the liquid living body phantoms of the embodiment 2 were made, all the time until 200 days passed.

As shown in Table 2, the liquid living body phantom of the embodiment 2 has small variations in its optical characteristics due to the preparation of the liquid living body phantom and has a good reproducibility.

In addition, as in the embodiment 1, the deviation rates of the optical characteristics of the prepared liquid living body phantoms from target values were also calculated in the embodiments 2 and 3. The calculation results are shown in Table 2.

As shown in Table 2, both of the deviations of the refractive index and the scattering coefficient of each of the liquid living body phantoms of the embodiment 2 and 3 from the target values are small and the liquid living body phantoms of the embodiment 2 and 3 have high reliability as a simulated organism.

COMPARATIVE EXAMPLE 1

Figure 11:
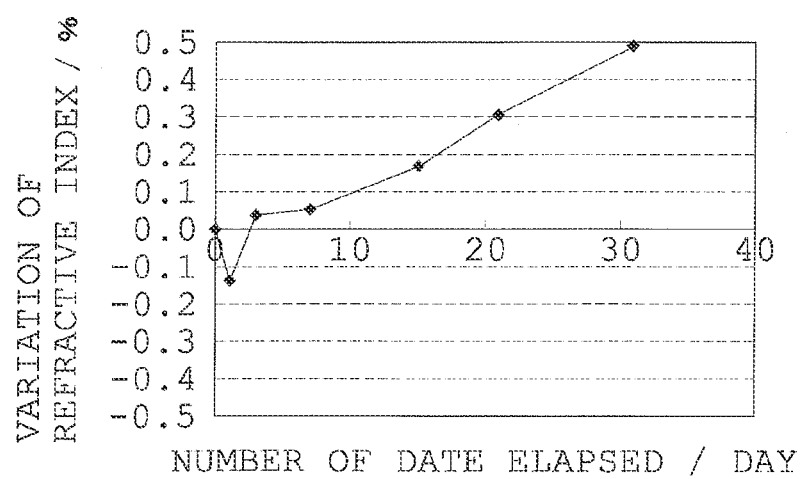
FIG. 11 is a graph showing a characteristic of a living body phantom of the comparative example 1 on variation of refractive index to elapsed days in the case where a prepared slide which is prepared with the living body phantom of the comparative example 1 as shown in FIG. 1 and in which the living body phantom of the comparative example 1 is put is placed at rest at room temperature.
Figure 12:
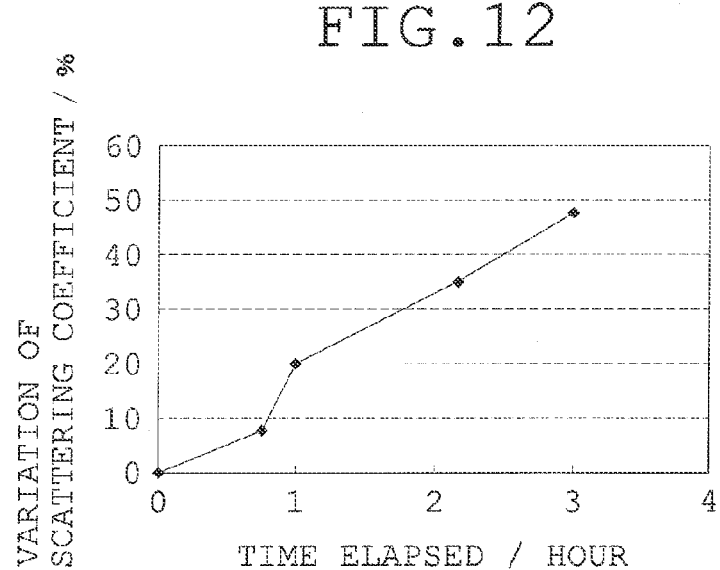
FIG. 12 is a graph showing a characteristic of the living body phantom of the comparative example 1 on variation of scattering coefficient to elapsed time in the case where a prepared slide which is prepared with the living body phantom of the comparative example 1 as shown in FIG. 1 and in which the living body phantom of the comparative example 1 is put is placed at rest at room temperature.
Figure 13:
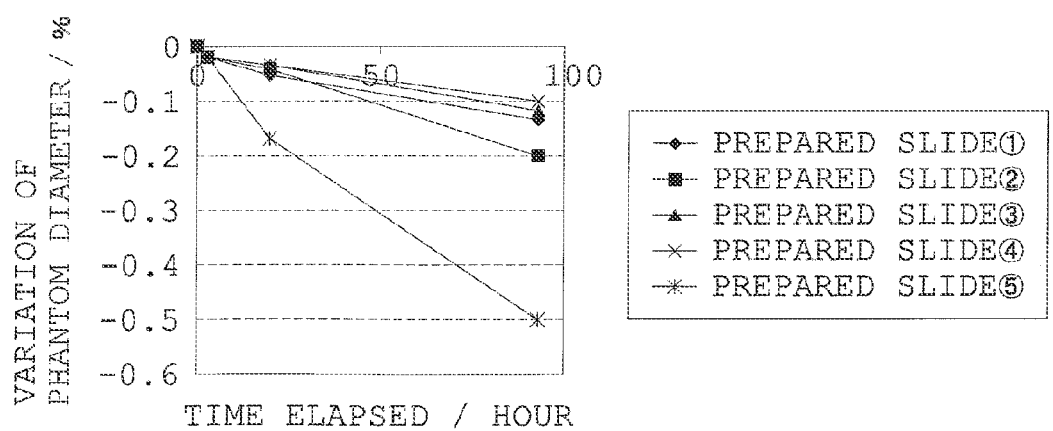
FIG. 13 is a graph showing a variation of the size of the living body phantom of the comparative example 1 to elapsed time in the case where a prepared slide which is prepared with the living body phantom of the comparative example 1 as shown in FIG. 1 and in which the living body phantom of the comparative example 1 is put is placed at rest at room temperature.

FIG. 11 is a graph showing a characteristic of a living body phantom of the comparative example 1 on variation of refractive index to elapsed days in the case where a prepared slide which is prepared with the living body phantom of the comparative example 1 as shown in FIG. 1 and in which the living body phantom of the comparative example 1 is put is placed at rest at room temperature. FIG. 12 is a graph showing a characteristic of the living body phantom of the comparative example 1 on variation of scattering coefficient to elapsed time in the case where a prepared slide which is prepared with the living body phantom of the comparative example 1 as shown in FIG. 1 and in which the living body phantom of the comparative example 1 is put is placed at rest at room temperature. FIG. 13 is a graph showing a variation of the size of the living body phantom of the comparative example 1 to elapsed time in the case where a prepared slide which is prepared with the living body phantom of the comparative example 1 as shown in FIG. 1 and in which the living body phantom of the comparative example 1 is put is placed at rest at room temperature. As shown in Table 1, the living body phantom of the comparative example 1 was made in the following manner using gelling agent instead of thickener. The gelling agent was added in such a way that the proportion of the mass of the gelling agent to the total mass of a solvent consisting of water, refractive index adjustment agent, and scattering body was 0.5 when the total mass of the solvent was 100, as in the embodiments 1 and 2.

Procedure for Making Phantom with Gelling Agent

The living body phantom of the comparative example 1 was made in the following manner:

(1') First, glycerin, water, and gelling agent are weighed in a sample bottle.

(2') Next, the sample bottle is heated and the materials in the sample bottle are stirred (at a temperature of 95° C.) until the gelling agent is dissolved.

(3') Next, a fluorescent substance body is added to the materials in the sample bottle in a plurality of batches and is mixed with the materials in the sample bottle. In this case, when the scattering body is a solvent dispersion type scattering body, the scattering body together with the material in the sample bottle is stirred at this point. When the scattering body is a powdery scattering body, the scattering body is weighed, is added to the materials in the sample bottle, and is stirred together with the material in the sample bottle, in the process (1').

(4') Next, a prepared slide 1 is made in such a way that: a solution of the living body phantom 4 with the gelling agent having undergone the process (3') is poured into a hole 3a provided for a silicon rubber 3 with which the upper plane of a glass slide 2 is coated and the thickness of which is about 2 mm, as shown in FIG. 1, before the solution of the living body phantom 4 gets cold and changes into a solid; and then the upper plane of the portion of the silicon rubber 3 into which the solution of the liquid living body phantom 4 is poured is covered with a cover glass 5.

Besides, the living body phantom of the comparative example 1 including gelling agent easily solidifies and it is difficult to take the living body phantom of the comparative example 1 stored in an airtight container from the airtight container to measure these living body phantoms. Accordingly, living body phantoms of the comparative example 1 were not put in airtight containers, and objects to be measured were targeted at only living body phantoms of the comparative example 1 which were put in prepared slides.

As in the embodiment 1, the refractive indices and the scattering coefficients of living body phantoms of the comparative example 1 were measured in order to examine the preservabilities of the living body phantoms of the comparative example 1 that were put in the prepared slides. In addition, the chronological change in the size of living body phantom of the comparative example 1 was also measured.

The measurement results of the refractive indices and the scattering coefficients of the living body phantoms of the comparative example 1 put in the prepared slides relative to elapsed days and elapsed time are shown in FIGS. 11 and 12 respectively, in the form of variation amount. And, the measurement results of the sizes of the living body phantoms of the comparative example 1 put in the prepared slides relative to elapsed time are shown in FIG. 13, in the form of variation amount. Besides, for the chronological change of the size of living body phantom of the comparative example 1, five living body phantoms which were put in prepared slides were made, and the size of each of the five living body phantoms was measured.

As shown in FIGS. 11 and 12, although the living body phantoms of the comparative example 1 including the gelling agent maintained the refractive indices and the scattering coefficients just after the living body phantoms of the comparative example 1 were made, the living body phantoms of the comparative example 1 began to contract after several hours passed. As shown in FIG. 13, a living body phantom of the comparative example 1 which had the maximum variation in size contracted to 50% of the size which the living body phantom had just after the living body phantom was made, after 90 hours passed from the preparation of these living body phantoms. And, the values widely varied every measurement, so that measurement values lacking reliability were obtained in the comparative example 1. Also, the living body phantoms of the comparative example 1 including the gelling agent became dry tablet-like phantoms after one week passed from after the preparation of the prepared slides.

Accordingly, it became impossible to use these phantoms of the comparative example 1 as a living body phantom, and it became impossible to measure the refractive indices and the scattering coefficients of these phantoms of the comparative example 1.

As described above, it was verified that: the chronological change of the living body phantom of the comparative example 1 including the gelling agent was large; and it was difficult to preserve the living body phantoms of the comparative examples 1 for a long time.

Also, the reproducibility of optical characteristics in living body phantoms that were made with the same composition and in the same preparation manner was also tested in the comparative example 1.

The detailed explanation is as follows. A plurality of living body phantoms (for example, five living body phantoms) for which a gelling agent was used, which had the composition shown in the comparative example 1, and which were put in prepared slides were made. The refractive indices and scattering coefficients of these living body phantoms each of which was put in a prepared slide and for which the gelling agent was used were measured as days passed.

And, the scattering coefficients of the living body phantoms of the comparative example 1 put in the prepared slides and including the gelling agent were measured until 3 hours passed just after the living body phantoms of the comparative example 1 were put in the prepared slides, and then the variation in the measured scattering coefficients relative to elapsed time was calculated. In addition, the refractive indices of the living body phantoms of the comparative example 1 put in the prepared slides and including the gelling agent were measured until 30 days passed just after the liquid living body phantoms of the comparative example 1 were put in the prepared slides, and then the variation in the measured refractive indices relative to elapsed days was calculated. The calculation results just after the living body phantoms of the comparative example 1 were made are shown in Table 2.

As shown in Table 2, in the variations in the optical characteristics of the living body phantoms of the comparative example 1 including the gelling agent due to the preparation of these phantoms, the variation in the refractive index of the living body phantom of the comparative example 1 is very large as compared with the liquid living body phantoms of the embodiments 1 to 3, and the living body phantom of the comparative example 1 has a bad reproducibility.

In addition, the deviation rates of the optical characteristics of the prepared living body phantoms from target values were also calculated in the comparative example 1.

The detailed explanation is as follows. The refractive indices and scattering coefficients which the living body phantoms of comparative example 1 including the gelling agent had just after the living body phantoms of the comparative example 1 were made were measured, and the deviation rates of the measured refractive indices and the measured scattering coefficients from target values were calculated when the refractive index and the scattering coefficient of a predetermined living body for which the living body phantoms of the comparative example 1 including the gelling agent were used as a simulated object were used as the target values. The calculation results are shown in Table 2.

As shown in Table 2, the scattering coefficient of the living body phantom of the comparative example 1 including the gelling agent widely deviates from the target value, and the living body phantoms of the comparative example 1 lacks reliability as a simulated organism.

TABLE 1

|  | Solvent: Mass Percentage (%) | | | Viscosity of Solution $\eta$ | Amount of Additive: Proportion of Mass of Additive to Mass of Solvent When Mass of Solvent Is 100 | | |
| --- | --- | --- | --- | --- | --- | --- | --- |
|  | Water | Glycerin | Scattering body |  | Thickener | Fluorescent Body | Gelling Agent |
| Embodiment 1 | 2 | 23 | 75 | 53.6 | 0.5 | 1 | — |
| Embodiment 2 | 22 | 25 | 53 | 51.2 | 0.5 | 1 | — |
| Embodiment 3 | 0 | 50 | 50 | 60.7 | 0.5 | 1 | — |
| Comparative Example 1 | 2 | 23 | 75 |  | — | 1 | 0.5 |

TABLE 2

|  | Deviation from Target Value (%) | | Variations in Preparation (%) | |
| --- | --- | --- | --- | --- |
|  | Refractive Index | Scattering Coefficient | Refractive Index | Scattering Coefficient |
| Embodiment 1 | 0.049 | 2.7 | 0.027 | 2.0 |
| Embodiment 2 | 0.001 | 1.4 | 0.001 | 1.1 |
| Embodiment 3 | 0.004 | 7.1 | — | — |
| Comparative Example 1 | 0.007 | 109 | 0.684 | 6.6 |

A liquid living body phantoms according to the present invention and a methods of making the same are useful not only for fields in which the performance of microscope objective lenses is estimated but also for every field in which living body phantoms are used.

What is claimed is:

1. A liquid living body phantom, which is used as a testing sample in a prepared slide in estimating performance of a microscope objective lens with an image of the testing sample in the prepared slide acquired by an imaging means via the microscope objective lens and with optical characteristics obtained from the image of the testing sample, comprising a non-gel solution having a viscosity, the non-gel solution at least including:
a solvent that at least includes water, a refractive index adjustment agent, and scattering bodies or a solvent that at least includes a refractive index adjustment agent and scattering bodies; and
a thickener, wherein an added amount of the thickener is a predetermined amount such that a proportion of a mass of the thickener to a mass of the solvent is in a range from 0.5% to 3%.

2. The liquid living body phantom according to claim 1, wherein the viscosity of the non-gel solution is in a ranqe from 40 mPa·s to 300 mPa·s at a temperature of 20° C.

3. The liquid living body phantom according to claim 1, wherein the viscosity of the non-gel solution is in a ranqe from 50 mPa·s to 100 mPa·s at a temperature of 20° C.

4. The liquid living body phantom according to claim 1, wherein the liquid living body phantom further includes a fluorescent substance.

5. The liquid living body phantom according to claim 4, wherein the fluorescent substance includes fluorescent microspheres.

6. The liquid living body phantom according to claim 5, wherein each of the fluorescent microspheres has the same particle diameter and the same shape as each of the scattering bodies does.

7. The liquid living body phantom according to claim 1, wherein, with respect to at least one of optical characteristics that include a refractive index, a scattering coefficient, an absorption coefficient, and an anisotropic scattering parameter, an optical characteristic quantity of the living body phantom is equivalent to an optical characteristic quantity of a living body.

8. The liquid living body phantom according to claim 1, wherein the scattering bodies are sphere-shaped particles.

9. The liquid living body phantom according to claim 1, wherein a particle diameter of each of the scattering bodies is in a range of 100 nm to 10 μm.

10. A method of making a liquid living body phantom comprising:
a first step of making a solvent by uniformly mixing water, a refractive index adjustment agent, and scattering bodies with one another or by uniformly mixing a refractive index adjustment agent and scattering bodies with each other, and
a second step of making a non-gel solution that has a viscosity in a range from 40 mPa·s to 300 mPa·s at a temperature of 20° C., by adding a predetermined amount of a thickener to the solvent made in the first step in such a way that a proportion of a mass of the thickener to a mass of the solvent is in a range from 0.5% to 3%.

11. The method of making a liquid living body phantom according to claim 10, wherein the non-gel solution is made to have a viscosity in a range from 50 mPa·s to 100 mPa·s at a temperature of 20° C. in the second step.

12. The method of making a liquid living body phantom according to claim 10 or 11, wherein a fluorescent substance is uniformly mixed with the water, the refractive index adjustment agent, and the scattering bodies or with the refractive index adjustment agent and the scattering bodies in the first step.

13. The method of making a liquid living body phantom according to claim 12, wherein the fluorescent substance includes fluorescent microspheres.

14. The method of making a liquid living body phantom according to claim 13, wherein each of the fluorescent microspheres has the same particle diameter and the same shape as each of the scattering bodies does.

15. The method of making a liquid living body phantom according to claim 10, wherein the scattering bodies are sphere-shaped particles.

16. The method of making a liquid living body phantom according to claim 10, wherein a particle diameter of each of the scattering bodies is in a range from 100 nm to 10 μm.

* * * * *